(12) United States Patent
Ram et al.

(10) Patent No.: US 10,070,806 B2
(45) Date of Patent: Sep. 11, 2018

(54) POSITION SENSOR, SENSOR ARRANGEMENT AND REHABILITATION DEVICE

(71) Applicant: TYROMOTION GMBH, Graz (AT)

(72) Inventors: David Ram, Graz (AT); Alexander Kollreider, Judendorf-Strassengel (AT); Harald Pitsch, Graz (AT); Valentin Cee, Eggersdorf (AT); Josef Neubauer, Hartberg (AT)

(73) Assignee: TYROMOTION GMBH, Graz (AT)

( * ) Notice: Subject to any disclaimer, the term of this patent is extended or adjusted under 35 U.S.C. 154(b) by 798 days.

(21) Appl. No.: 14/363,691

(22) PCT Filed: Dec. 7, 2012

(86) PCT No.: PCT/EP2012/074813
§ 371 (c)(1),
(2) Date: Aug. 15, 2014

(87) PCT Pub. No.: WO2013/083788
PCT Pub. Date: Jun. 13, 2013

(65) Prior Publication Data
US 2014/0350437 A1    Nov. 27, 2014

(30) Foreign Application Priority Data
Dec. 9, 2011 (DE) .......................... 10 2011 056 219

(51) Int. Cl.
*A61B 5/103* (2006.01)
*A61B 5/11* (2006.01)
(Continued)

(52) U.S. Cl.
CPC .......... *A61B 5/1124* (2013.01); *A61B 5/1126* (2013.01); *B65H 49/02* (2013.01); *G01B 5/004* (2013.01)

(58) Field of Classification Search
CPC ................ G06F 3/0414; G06F 3/0485; B60Y 2400/301
(Continued)

(56) References Cited

U.S. PATENT DOCUMENTS 4,703,443 A * 10/1987 Moriyasu ................... B25J 9/00
33/1 N
5,035,064 A * 7/1991 Care ..................... G01B 3/1061
33/760
(Continued)

FOREIGN PATENT DOCUMENTS

CN          2569795 A      9/2003
CN          1483996 A      3/2004
(Continued)

OTHER PUBLICATIONS

German Office Action in related German Patent Application No. 10 2011 056 219.2, dated Sep. 22, 2014.
(Continued)

*Primary Examiner* — May Abouelela
(74) *Attorney, Agent, or Firm* — Greenblum & Bernstein, P.L.C.

(57) ABSTRACT

Position sensor having a holder, a force measuring device permanently connected to the holder, and a winding device, which is permanently connected to the force measuring device and has a drive having an electric motor. Winding device is configured to unwind and wind a cable and to determine an unwinding length of the cable. Guide device permanently connected to the holder has a centering device for passing through the cable, an outlet apparatus which is mounted on universal joints and is intended to pass through the cable with a variable direction, and a position sensor for determining an angular position of the outlet apparatus. Position sensor is set up to determine position of a prede-
(Continued)

Figure 1:
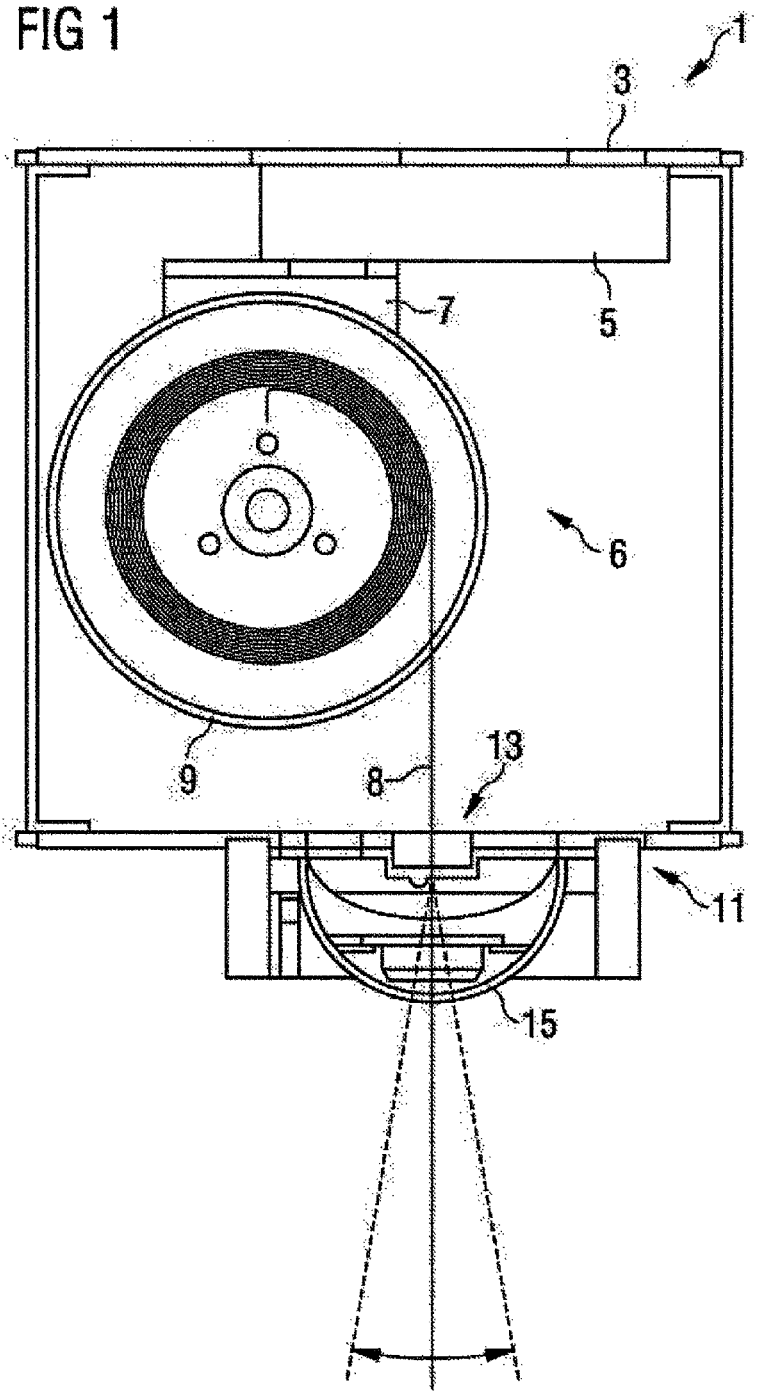

termined point of the cable relative to holder on the basis of determined angular position and unwinding length.

14 Claims, 4 Drawing Sheets

(51) Int. Cl.
 *B65H 49/02* (2006.01)
 *G01B 5/004* (2006.01)
(58) Field of Classification Search
 USPC .................. 600/587, 595; 428/1; 33/1 N
 See application file for complete search history.

(56) References Cited

U.S. PATENT DOCUMENTS

| | | | | |
|---|---|---|---|---|
| 6,481,272 | B1* | 11/2002 | Kieselbach | B62D 15/02 116/31 |
| 6,768,321 | B2* | 7/2004 | Wain | B60N 2/0224 242/563 |
| 6,785,973 | B1* | 9/2004 | Janssen | G01B 5/004 33/1 N |
| 7,118,094 | B2* | 10/2006 | McDaniel | B66D 1/36 254/335 |
| 7,395,609 | B2* | 7/2008 | Powell | G01B 5/008 33/1 N |
| 7,651,442 | B2* | 1/2010 | Carlson | A63B 21/0083 482/1 |
| 7,665,223 | B2* | 2/2010 | Swanson | E04F 21/0076 33/701 |
| 2004/0097330 | A1 | 5/2004 | Edgerton et al. | |
| 2004/0176226 | A1 | 9/2004 | Carlson | |
| 2006/0094569 | A1* | 5/2006 | Day | A63B 21/015 482/57 |
| 2007/0060445 | A1* | 3/2007 | Reinkensmeyer | A61H 1/0274 482/1 |
| 2007/0155588 | A1* | 7/2007 | Stark | A61F 5/0102 482/8 |
| 2009/0017993 | A1 | 1/2009 | Khanicheh et al. | |
| 2011/0126416 | A1* | 6/2011 | Swanson | G01B 5/004 33/527 |

FOREIGN PATENT DOCUMENTS

| | | |
|---|---|---|
| CN | 102088945 Y | 6/2011 |
| DE | 2502809 | 7/1976 |
| DE | 20216563 | 1/2003 |
| DE | 102004023981 | 12/2005 |
| DE | 102005013122 | 2/2007 |
| EP | 1219918 | 7/2002 |
| WO | WO2010/147574 | 12/2010 |

OTHER PUBLICATIONS

German Office Action in related German Patent Application No. 10 2011 056 219.2, dated May 9, 2012.

Office Action issued in China counterpart Patent Appl. No. 20120069339.6, dated Mar. 30, 2016, along with an English translation thereof.

Office Action issued in China counterpart Patent Appl. No. 20120069339.6, dated Jan. 26, 2017, along with an English translation thereof.

Office Action issued in China counterpart Patent Appl. No. 20120069339.6, dated Jul. 20, 2017, along with an English translation thereof.

* cited by examiner

POSITION SENSOR, SENSOR ARRANGEMENT AND REHABILITATION DEVICE

The invention concerns a position sensor, a sensor arrangement based on such a position sensor, and a rehabilitation device based on such a position sensor.

Rehabilitation devices, in particular for patients with reduced functionality of the upper extremities, in some embodiments feature a position sensor to determine the position of the extremity of the patient. For that, such a position sensor comprises for example a cable system featuring at one end of the part a loop or a sling that is intended to hold the extremity of the patient, for example an arm. As an example, a weight system guides the cable via a roller, whereby the weight system provides a strain relief for the arm of the patient. To determine a position of the arm, a certain cable length is determined in the cable system, for example, and additionally, a camera is utilized to calculate the position based on the camera signal and the calculated length of the cable.

One objective that needs to be solved consists in providing an improved concept to determine a position that can be used particularly in a therapy device.

This objective is solved by the object of the independent patent claims. Further embodiments and design forms are the object of the dependent claims.

The proposed solution is based on the idea that a cable can be unwound and wound up via a winding device with an electric drive, whereby the winding up and unwinding simultaneously determine an unwinding length of the unwound cable. The cable is guided away from the winding device via a guiding device, whereby the guiding device features a fixed centering device and a gimbal-mounted outlet apparatus. A position sensor on the flexible outlet apparatus can thereby determine an outlet angle of the cable. Based on the determined unwinding length and the exit angle of the cable, the position sensor is thereby set up to determine the position of a pre-determined point of the cable, for example, the end of the cable which is attached to a loop.

Based on this concept, the proposed solution allows to determine the position in a highly accurate manner and with a comparatively small spatial requirement. The force measuring device and the electric drives make it possible to apply a specific adjustable force onto the cable or onto an object attached to the cable.

When two such position sensors are combined, the position of an object in the room that is attached to the cable can with very little effort be determined based on the calculated room positions of the respective cable points. Such position sensors are therefore particularly well-suited for a therapy device, which is attached to or rather holds an arm in two loops at the end points of the cables, for example to capture and graphically visualize the position of the arm.

In one embodiment a position sensor incorporates a holder, a force measuring device with a fixed connection to the holder, and a winding device with a fixed connection to the force measuring device featuring a drive with an electric motor. The winding device is designed for the unwinding and winding of a cable and for determining an unwinding length of the unwound cable. The position sensor further incorporates a guiding device with a fixed connection to the holder, featuring a centering device in particular for the defined passing through of the cable in a fixed direction, a gimbal-mounted outlet apparatus for the passing through of the cable in a variable direction, and a position sensor to determine an angular position of the outlet apparatus. Based on the determined angular position and the unwinding length, the position sensor is designed to determine the position of a predefined point of the cable relative to the holder. The electric motor is set up to act on the cable with an adjustable tensile force, which is set based on a force which acts on the holder via the cable and which is determined by the force measuring device.

The guiding device facilitates the precise determination of the angular position of the cable in the room. It is possible, in particular due to the two defined feed-through passages of the cable, via the guiding device, namely in the centering device and the outlet apparatus, to calculate a location vector or direction vector for the direction of the cable outside of the position sensor. In this case, the feed-through in the centering device is a fixed defined point, while the feed-through through the outlet apparatus provides a variable point due to the gimbal mounting. Based on these two points, it is possible to calculate the position vector with known procedures from vector geometry. The accuracy of the calculation is based on the fact that an exact orientation of the outlet apparatus can be determined via the position sensor. For example, the position sensor incorporates one or multiple acceleration sensors, which enable an angular position of the outlet apparatus and thereby a determination of the point of the feed-through for the cable in the outlet apparatus.

Based on the calculated position vector and the unwinding length of the cable, it is possible to calculate the position of the pre-determined point of the cable in the room or relative to the holder or to the position sensor. For that it is only necessary to know the distance of the predefined point to the position sensor and a reference state with a specific unwinding length. It can for example be set through the programming or the configuration of the position sensor. For example, an encoder is intended to determine the unwinding length on the winding device, which counts the number of rotations of a spool, whereby also partial rotations can be incorporated in the calculation with a predefined accuracy. Based on this rotation number, which can also be a non-integer number, it is possible to determine the unwinding length through the radius of the spool or through the winding radius. In order to be able to determine the unwinding length as accurately as possible, the winding device is preferably designed in such a manner that the cable is wound up in one parallel layer, and thus with a constant winding radius, or stacked in one layer, meaning with a continuously rising winding radius. However, for thinner cable strengths a sufficiently high accuracy for the determination of the unwinding length can also be achieved with any winding type, through the assumption of a mean winding radius for example.

In different embodiments, the drive also features its own winding spring, which contributes for example to an automatic winding of the cable with a specified force. Alternatively or in addition, the drive can also feature an electric motor, which powers the spool of the winding device. As an example, the electric motor is set up to apply an adjustable tensile force on the cable. Correspondingly, a load attached to the cable will be pulled up with this force. This results, for example, in that the cable unwinds when the load has a higher pull-down force than the set force of the motor. On the other hand, the cable is wound if the load attached to the cable applies a lower force than the force set by the motor.

As an example, the tensile force of the electric motor is set based on a force, which acts on the holder via the cable and which is determined by the force measuring device. Thus, for example, the load attached to the cable can be held in an at rest position. Furthermore, it is possible, for example, in a calibration phase, to specify the force of the load that acts on the cable to then use it as a basis to set the tensile force of the motor. Thus, load changes in a positive and negative direction on the cable lead to an unwinding or winding of the cable through the winding device.

When utilizing an electric motor for the drive, the unwinding length can be determined for example via a motor encoder that is connected with the electric motor. For that, in some embodiments, the motor features position sensors or rotation sensors, which determine a position of the motor. Alternatively or in addition, electric parameters can also be analyzed during the operation of the motor in order to monitor a rotation angle of the motor.

Thanks to the gimbal mounting of the outlet apparatus, it is possible that it can be moved or turned at least along two room axes. The angular position of the outlet apparatus in particular can be illustrated by two room angles, an azimuth angle and an elevation angle, whereas the azimuth angle covers an angle range from about 0° to about 360° and the elevation angle covers an angle from about 0° up to about 180° or from about −90° up to about +90°. Based on these angles and the known point of the direction-variable feed-through for the cable, the variable feed-through point can thereby be used to determine the position vector or the direction vector of the cable. When the point of the feed-through in the centering device lines up with the pivotal center of the outlet apparatus, the direction vector of the cable corresponds directly with the angle position of the outlet apparatus for example.

A position sensor in one of the described embodiments can, for example, be utilized for a rehabilitation device or a therapy device, whereby on the predefined point of the cable a loop or a sling is intended by which an extremity, in particular a patient's arm, can be held. Due to the adjustable force or the force measuring, the extremity of the patient can thereby be relieved so that the patient requires less internal strength to hold the extremity, in particular the arm. The determination of the position of the predefined point or the loops or sling make it possible to track the movement of the patient and visualize it graphically for example. Since no external components, such as a camera, are necessary on the position sensor to determine an exact position, such a therapy device or rehabilitation device can be manufactured or installed and operated at a low cost.

In different embodiments, several of these position sensors can be combined as well. For example, one embodiment of a sensor arrangement incorporates a first and a second position sensor in accordance with one of the described embodiments, whereas the first position sensor and the second position sensor are arranged in a joint holder. Through that in particular, the respective force measurement devices and the guiding devices of the two position sensors are firmly connected with a joint holder. For example, in this case, the holder of the first position sensor also serves as the holder of the second position sensor.

In different embodiments, additional position sensors can also be integrated in the sensor arrangement, which in turn are based on the previously described exemplary embodiments.

Nevertheless, with each of the position sensors the position of the respectively predefined point on the respective cable can be determined independently from each other. It is therefore possible, based on the determined points in the room of the two cables, to determine the position of an object relative to the joint holder, which is mounted at the predefined point of the cable of the first position sensor and the predefined point of the cable of the second position sensor. In particular, again through known vector-geometric calculations, it is, for example, possible based on the two specific room points to calculate a position vector for the position of the object in the room or relative to the holder.

In additional embodiments, the sensor arrangement is set up on the premise to visualize the position of the object graphically on a display device. To achieve this, the sensor arrangement can, for example, incorporate a calculation unit and the display device. Such a calculation unit can, for example, also be provided by a standard computer that is connected with the position sensors.

In different embodiments of the sensor arrangements, a sling or loop to carry an extremity of a person or an animal, in particular an arm, is intended on the predefined point of the cable of the first position sensors and the predefined point of the cable of the second position sensor.

For example, in addition to the visualization of the object, in particular an arm, an illustration of a virtual reality can also take occur, for which, controlled by the movement of the arm or the extremity, actions can be triggered or objects can be manipulated in the virtual reality.

A sensor arrangement of the described type can in turn be utilized in particular for a therapy device or rehabilitation device holding or fastening an arm of a patient in two slings or loops. Such sensor arrangements can also be combined to hold both arms of a patient at the same time for example. Correspondingly, an/one embodiment of a rehabilitation device incorporates, for example, at least two sensor arrangements in accordance with the previously described embodiments.

With such a rehabilitation device or therapy device it is made easier for patients with reduced functionality of the upper extremity to carry out and re-learn movements. In this case, the patient is connected at two points of the arm via the slings or loops, for example at the wrist and at elbow, with the cables of the therapeutic device. As previously described, it is possible through the cables of the position sensors to fully or partially relieve the arm of the patient from force of gravity by pulling the arm up with an adjustable force. The upward pull is generated by the separate winding devices, which are actively powered and/or powered by a spring load. Through the attachment of the winding devices or the drives at the holder or a housing of the device and the force measuring device in between, it is possible to permanently and continuously measure the force with which the patient counteracts the lifting of the arm, or rather with which the arm of the patient pulls down. This also makes it possible to respond dynamically to the behavior of the patient and to add an intelligent behavior to the device, for example, through the variation of the tensile force of the winding device.

Due to the weight relief and the force measurements, a therapy device in accordance with the described embodiments provides the opportunity at any time to reconstruct the exact position of the arm, in particular the lower arm of the patient. This information, as described above, can be utilized for a visualization of the arm on a monitor.

By utilizing cables, it is possible during the therapy to utilize the entire room in front of the patient for therapy without being limited by the device itself; a sensor arrangement in one of the described embodiments can each treat one arm, respectively. Through the coupling of two similar or identical systems, a two-arm operation is also made possible. The design of the utilized position sensors in accordance with the described embodiments enable the complete determination of the position of the arm, in contrast to common therapy devices or position sensors, for which additional, external sensors, such as cameras, are necessary. The analysis of the force that is applied to the position sensors via the patient's arm facilitates a regulation of the weight relief for the patient's arm. A sensor arrangement in accordance with the described embodiments can be suspended in different design forms, for example with its own frame, an installation on a ceiling, an installation above a hospital bed or similar.

The invention is explained in detail through the figures below using several exemplary embodiments. Here, identical reference symbols mark elements or components with the same function. To the degree that switch parts or components correspond with respect to their function, their description is not repeated in any of the following figures.

The following is shown:

FIG. 1 an exemplary embodiment of a position sensor

Figure 2:
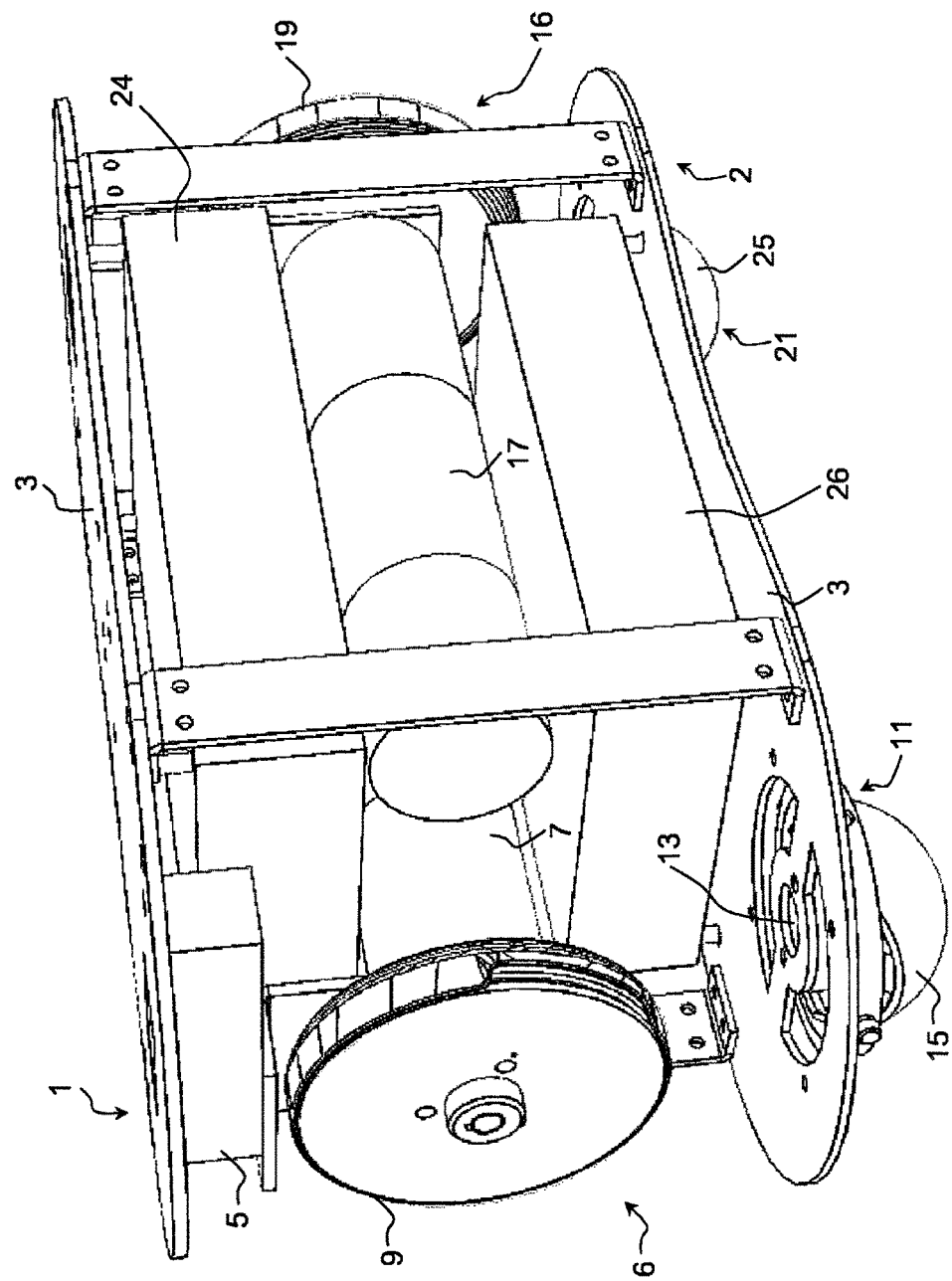

FIG. 2 an exemplary embodiment of a sensor arrangement

FIG. 3 detailed views of an embodiment of a guiding device, and

Figure 4:
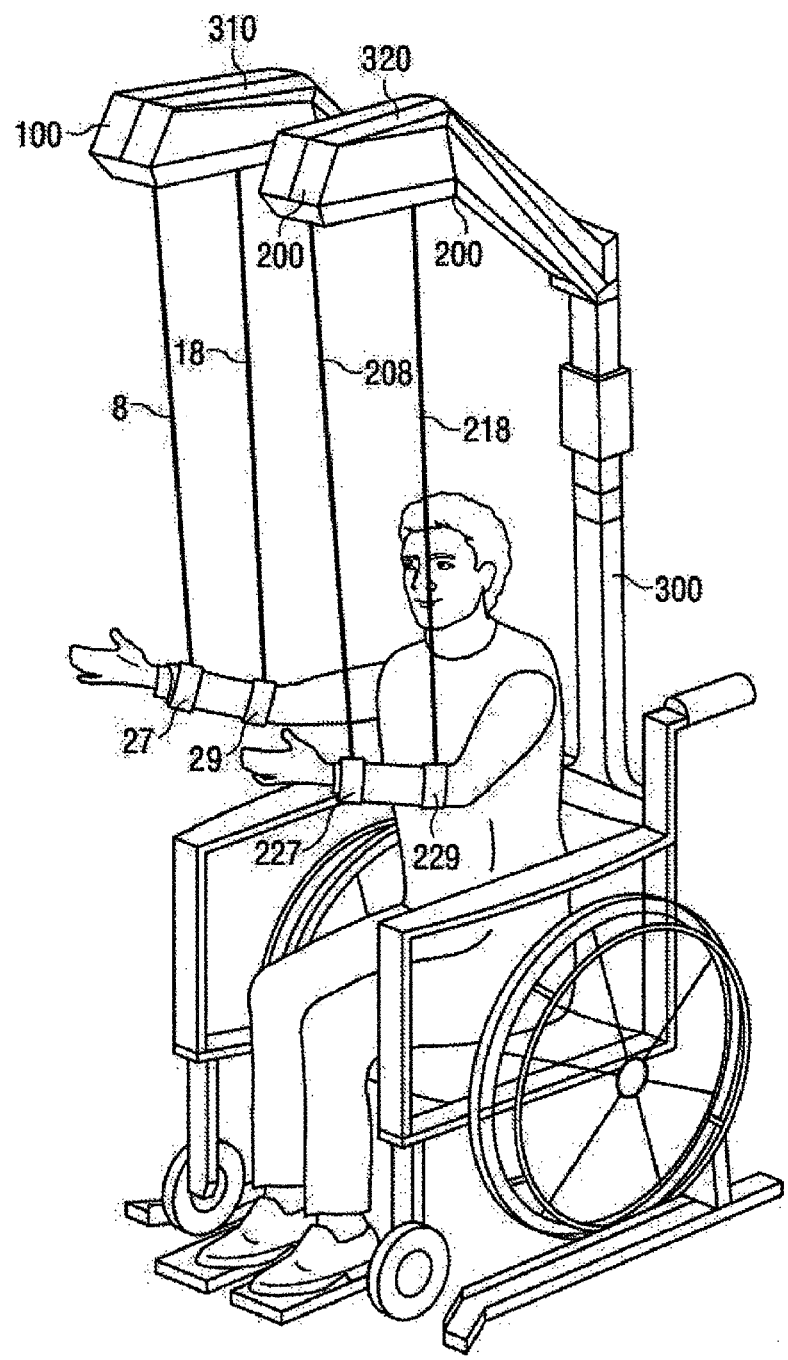

FIG. 4 an embodiment of a rehabilitation device.

FIG. 1 shows an embodiment of a position sensor 1 with a holder 3 or a housing. In holder 3, a winding device 6 is arranged with a drive 7 and a spool 9, which is connected with the holder 3 via a measuring device 5. Via the force measuring device 5, the force acting between the winding device 6 and the holder 3 can thereby be measured.

Furthermore, on the holder 3, a guiding device 11 is firmly connected, which features a centering device 13 and a gimbal-mounted outlet apparatus 15. Through the centering device 13, in particular through the center point of the centering device 13, a cable 8 wound on the spool 9 is passed through centrally and with a fixed location or rather a fixed direction. The cable 8 will furthermore be guided through the center point of the outlet apparatus 15, whereby, due to the gimbal mounting of the outlet apparatus 15, an orientation of the outlet apparatus is adjustable. For example, changing the tensile force direction to the cable 8, illustrated with the dashed lines, at an angle to the vertically running line of the cable 8, changes an angular position of the outlet apparatus.

The guiding device 11 also features a position sensor, not illustrated here for clarity purposes, which allows the determination of the angular position of the outlet apparatus 15. The position sensor is preferably arranged on the inside of the outlet apparatus 15. Based on the determined angular position of the outlet apparatus 15, which can be illustrated through an azimuth angle and an elevation angle for example, a position of the point for the feed-through in the outlet apparatus 15 can be determined. Based on this point of the feed-through of the outlet apparatus 15 and the point of the feed-through of the cable 8 through the centering device 13, a direction vector can be determined, which corresponds with the exit direction of the cable 8 from the position sensor 1. This can be calculated with known vector-geometry procedures.

If the outlet apparatus is designed in a spherical shape and the feed-through point of the centering device 13 corresponds with the center point of this sphere, the angle position or rather the slope of the outlet apparatus 15 can be utilized directly as a direction vector of the cable 8 that is exiting from the position sensor 1.

On the winding device 6, corresponding sensors are intended, which register a rotation of the spool 9, so that from a number of rotations of the spool 9 the length of the unwound cable can be determined based on a starting length.

For the embodiment at hand, the cable 8 is wound in one layer on the spool 9 so that the cable is wound in a stacked manner and not in a parallel manner. Correspondingly, depending on the determined rotation number of the spool 9 and the rotation-dependent dependent winding radius, the unwinding length of the cable can be calculated. Alternatively, the cable 8 can also be wound in one, parallel layer on a spool.

Based on this unwinding length and the previously calculated angle or rather the position vector of the exiting cable 8, a position of a predefined point of the cable 8 in the room or rather relative to the holder 3 can be calculated. For that, the position sensor 1 features, for example, a not illustrated analysis device with respective electronics, which carries out the necessary calculations. For example, a digital signal processor or an application-specific integrated circuit, ASIC, can be utilized for this purpose.

Furthermore, via the force measuring device 5, the force that acts on the holder 3 via the cable 8, can be calculated in particular. Furthermore, the drive 7, for example an electric motor, can control an adjustable tensile force acting on the cable 8. In particular, this tensile force can be adjusted based on the force onto the cable 8 calculated via the force measurements device. The tensile force can be adjusted during the operation of the position sensor 1, but can also be firmly set based on a calibration phase, which can also be repeated. For example, a sling or loop can be attached to the cable, which holds the arm of a patient. In the calibration phase, the force of the arm in an idle position that is applied to the holder 3, can be calculated in order to subsequently set this calculated force as the tensile force of the drive 7. Correspondingly, the arm of the patient is relieved by this set tensile force, so that movements of the arm can be carried out using less force.

FIG. 2 shows an embodiment of a sensor device with a first position sensor 1 and a second position sensor 2, each based on the embodiment of a position sensor illustrated in FIG. 1. Correspondingly, the second position sensor 2 also features the winding device 16 with a spool 19 and a drive 17, which are connected via a force measuring device, which is not visible here, with a joint holder 3. In addition, the second position sensor 2 features a guiding device 21, of which only the gimbal-mounted guiding device 25 is visible.

The sensor arrangement further incorporates a power supply unit 24 and an electronic system 26, which are set up to control the winding devices 6, 16 and to analyze the corresponding measurements data.

Via the sensor arrangement, two respective cables can be controlled independently from each other, or their unwinding length and their exit angle can be calculated in order to determine the respective position of a predefined point on the corresponding cable.

For example, the cables not illustrated here are intended to feature loops or slings, which can hold the arm of a patient. As previously described in the embodiment in FIG. 1, a respectively predefined point, namely the attachment point of the sling or loop, can be calculated for the two position sensors. Based on these two points, it is possible to calculate a vector in the room, which, for example, reflects the position of a lower arm of the patient in the room. The loops or slings on the cables are attached at the wrist and on the elbow of the patient for example. The information about the spatial positioning of the patient's lower arm are utilized, for example, to display a visualization of the arm on a monitor and thereby control an artificial reality and to manipulate objects here. For that, the sensor arrangement is connected for example to a computer featuring respective software. Additionally or alternatively to the illustrated electric motors 7, 17, the drive can also feature a winding spring, which applies a defined force onto the spools 9, 19 and thereby the cables.

Figure 3A:
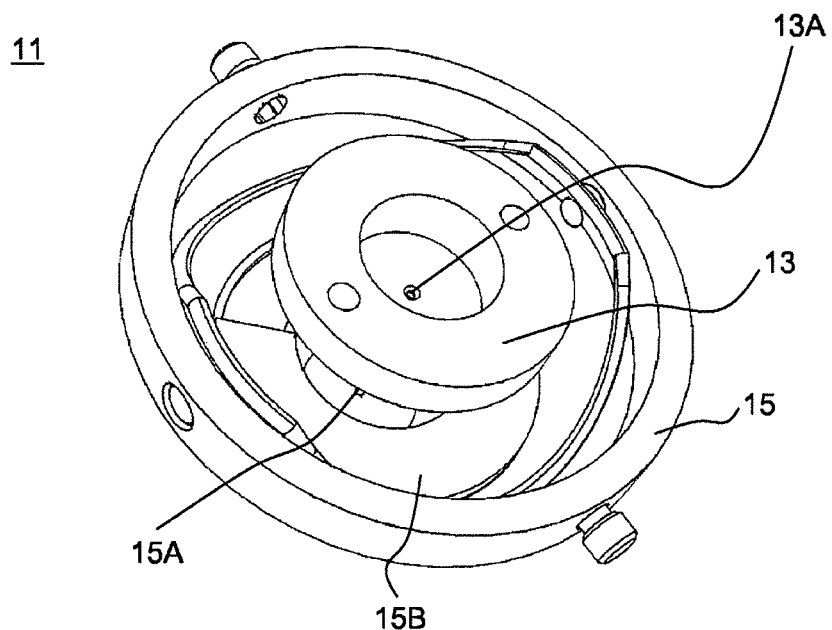
Figure 3B:
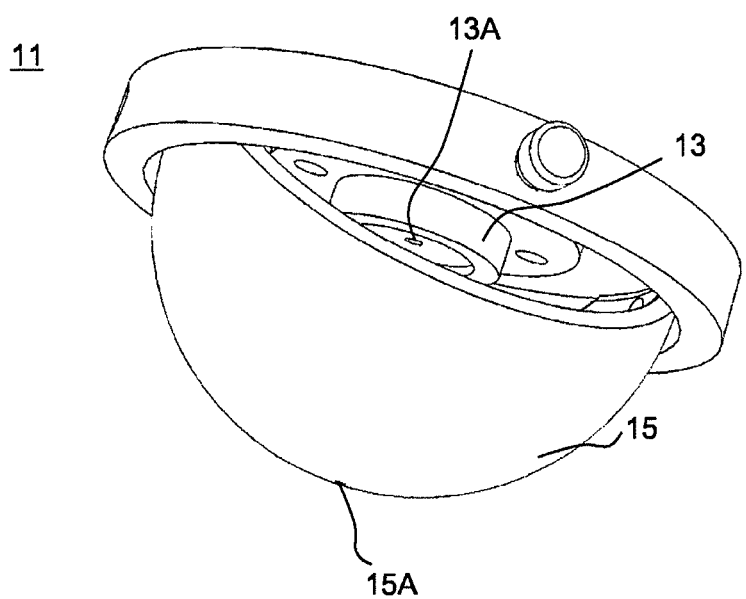

FIG. 3 shows different perspective views of an embodiment of a guiding device 11, whereas FIG. 3A shows a diagonal view from the top and FIG. 3B shows a diagonal view from the bottom. The guiding device 11 in this case incorporates the centering device 13 with a centrally positioned hole 13A to feed the cable through. Furthermore, the gimbal-mounted outlet apparatus 15 is illustrated, which is rotatable along two axes in accordance with the gimbal mounting. The centering device 13 remains in place even with a pivotal motion of the outlet apparatus. The outlet apparatus 15 also features a hole 15A to pass through the cable, whereas through a corresponding impact of a force on the cable, the position of the hole 15A is changed and the angular position of the outlet apparatus 15 is thereby modified. The exact angular position can be determined with an intended position sensor 15B located on the inside of the outlet apparatus 15. For example, this position sensor 15B is comprised of one or multiple acceleration sensors, which determine the acceleration and different orientations in order to determine an angular position. Such a position sensor can also be referred to as a gyroscopic sensor. FIG. 3B shows in particular the half-sphere shaped design of the outlet apparatus 15 with the outlet hole 15A.

The sensor arrangement illustrated in FIG. 2 can be utilized for example for a therapy device or rehabilitation device which makes it easier for patients with reduced functionality of the upper extremities to carry out or relearn movements. This is achieved in particular through the full or partial relief of the gravitational strain on the arm of the patient. Furthermore, the integrated positioning of the previously described loops or slings can determine, and if necessary record, a kinetic behavior of the patient or respectively the arm of the patient. The kinetic data and position data of the arm can, for example, be graphically visualized to motivate the patient in order to animate him to carry out certain movements within the framework of a virtual reality for example.

While the sensor arrangement illustrated in FIG. 2 can be utilized for the therapeutic treatment of an individual arm, a respective combination of two such sensor arrangements also enables a two-arm operation. FIG. 4 shows an exemplary embodiment of the therapy device, for which a first and second therapy device 100, 200 is utilized for the right and respectively left arm of a patient. The sensor arrangements 100, 200 are for example attached to the corresponding holders 310, 320 of a frame 300, which in the illustrated embodiment is attached to a wheelchair carrying the patient. From the sensor arrangements 100, 200 the corresponding cables 8, 18 or rather 208, 218 run to the right or respectively left arm of the patient. In particular, the right arm is held by the slings 27, 29 while the right arm is held by the slings 227, 229.

Instead of the wheelchair, a frame 300 can also be attached to a hospital bed or a common chair. Through the use of the cables 8, 18, 208, 218 it is possible during the therapy to utilize the entire room in front of the patient for the therapy treatment without being limited by the device itself. In particular, all necessary sensors that are required to determine the position of the arm are integrated in the corresponding sensor arrangements 100, 200, in contrast to common systems which use a camera to determine the position for example.

The analysis of the force of the patient arm enables a corresponding regulation of the weight relief, which can be designed differently for the right and left arm in particular.

The analysis of the measurable variables can take place within the corresponding sensor arrangements but also in a computing unit connected with the sensor arrangements 100, 200 such as a computer or a notebook for example.

The invention claimed is:

1. A rehabilitation device comprising at least one position sensor, the at least one position sensor comprising:
    a holder;
    a force measuring device connected to the holder, wherein the force measuring device is operable to determine a force pulling on the holder by a user in the rehabilitation device;
    a winding device, with a drive, connected to the force measuring device, wherein the drive includes an electric motor, the winding device configured to unwind and wind a cable and operable to determine an unwinding length of the unwound cable; and
    a guiding device connected to the holder, wherein the guiding device includes a centering device for a defined, fixed-direction passing through of the cable, a gimbal-mounted outlet apparatus for a variable-direction passing through of the cable, and an angular position sensor operable to determine an angular position of the outlet apparatus;
    wherein the at least one position sensor is configured to determine a position of a predefined point of the cable relative to the holder based on the determined angular position and the unwinding length; and
    wherein the electric motor is configured to pull on the cable with an adjustable tensile force, which is adjusted based on the determined force which pulls on the holder via the cable by the user.

2. The rehabilitation device in accordance with claim 1, wherein the winding device is configured so that the cable is wound up in one parallel layer or stacked in one layer.

3. The rehabilitation device in accordance with claim 1, wherein the drive comprises a winding spring.

4. The rehabilitation device in accordance with claim 1, where the unwinding length is determined via a motor encoder that is connected to the electric motor.

5. The rehabilitation device in accordance with claim 1, where the at least one position sensor includes at least one acceleration sensor.

6. The rehabilitation device in accordance with claim 1, where the winding device is set up to unwind and wind the cable based on a change of the force determined by the force measuring device.

7. The rehabilitation device in accordance with claim 1, wherein the at least one position sensor comprises a first position sensor and a second position sensor in a sensor arrangement, in which the first position sensor and the second position sensor are arranged in a joint holder.

8. The rehabilitation device in accordance with claim 7, wherein the holder of the first position sensor is also the holder of the second position sensor.

9. The rehabilitation device in accordance with claim 7, wherein the sensor arrangement is configured to calculate a position of an object relative to the joint holder based on a first position of a first predefined point of the cable of the first position sensor and a second position of a second predefined point of the cable of the second position sensor.

10. The rehabilitation device in accordance with claim 9, wherein the device is configured to graphically visualize the position of the object on a display device.

11. The rehabilitation device in accordance with claim 9, wherein the sensor arrangement is configured to calculate the position of the object as a position vector of the object in a room.

12. The rehabilitation device in accordance with claim 7, where at the first predefined point of the cable of the first position sensor and the second predefined point of the cable of the second position sensor respectively a sling or loop is arranged to hold an extremity of a person or an animal.

13. The rehabilitation device in accordance with claim 12, wherein the device comprises at least two sensor arrangements.

14. The rehabilitation device in accordance with claim 12, wherein the sling or the loop is configured to hold an arm of the person or the animal.

* * * * *